(12) United States Patent
Jiang et al.

(10) Patent No.: US 8,043,454 B1
(45) Date of Patent: Oct. 25, 2011

(54) METHOD OF FORMING HERMETIC VIAS UTILIZING METAL-METAL OXIDES

(75) Inventors: Guangqiang Jiang, Valencia, CA (US); Attila Antalfy, Santa Clarita, CA (US); Gary D. Schnittgrund, Granada Hills, CA (US)

(73) Assignee: Alfred E. Mann Foundation For Scientific Research, Santa Clarita, CA (US)

( * ) Notice: Subject to any disclaimer, the term of this patent is extended or adjusted under 35 U.S.C. 154(b) by 0 days.

(21) Appl. No.: 12/987,851

(22) Filed: Jan. 10, 2011

Related U.S. Application Data

(62) Division of application No. 11/694,774, filed on Mar. 30, 2007, now Pat. No. 7,901,761.

(60) Provisional application No. 60/744,992, filed on Apr. 17, 2006.

(51) Int. Cl.
*C03B 29/00* (2006.01)

(52) U.S. Cl. ............... 156/89.11; 156/89.12; 156/89.16
(58) Field of Classification Search ............. 156/89.11, 156/89.12, 89.16
See application file for complete search history.

(56) References Cited

U.S. PATENT DOCUMENTS

| | | | | |
|---|---|---|---|---|
| 5,855,711 | A * | 1/1999 | Araki et al. | 156/89.16 |
| 6,432,239 | B1 * | 8/2002 | Mandai et al. | 156/89.12 |
| 7,084,350 | B2 * | 8/2006 | De La Prieta et al. | 174/169 |

* cited by examiner

*Primary Examiner* — Cathy Lam
(74) *Attorney, Agent, or Firm* — Gary D. Schnittgrund

(57) ABSTRACT

The invention is a method of making a hermetic via in a ceramic substrate that is comprised of noble metal powder in a glass-free paste that contains an admixture of a particulate phase of niobium pentoxide. The electrically conductive platinum provides excellent electrical conductivity while the niobium pentoxide phase prevents shrinkage of the paste during thermal processing and binds to both the ceramic and the noble metal particulates in the via, thus maintaining a hermetic seal around the via.

3 Claims, 1 Drawing Sheet

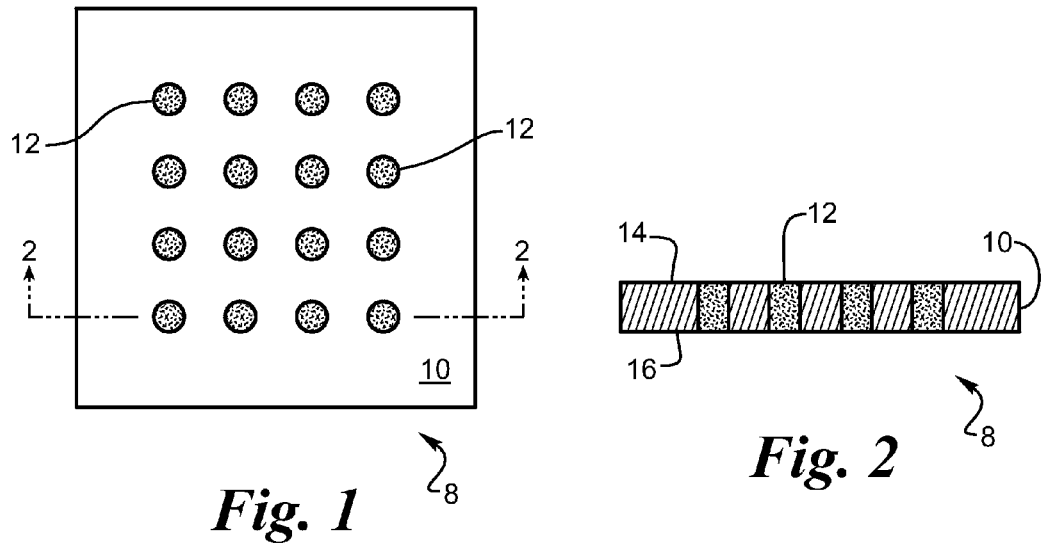
Fig. 1
Fig. 2
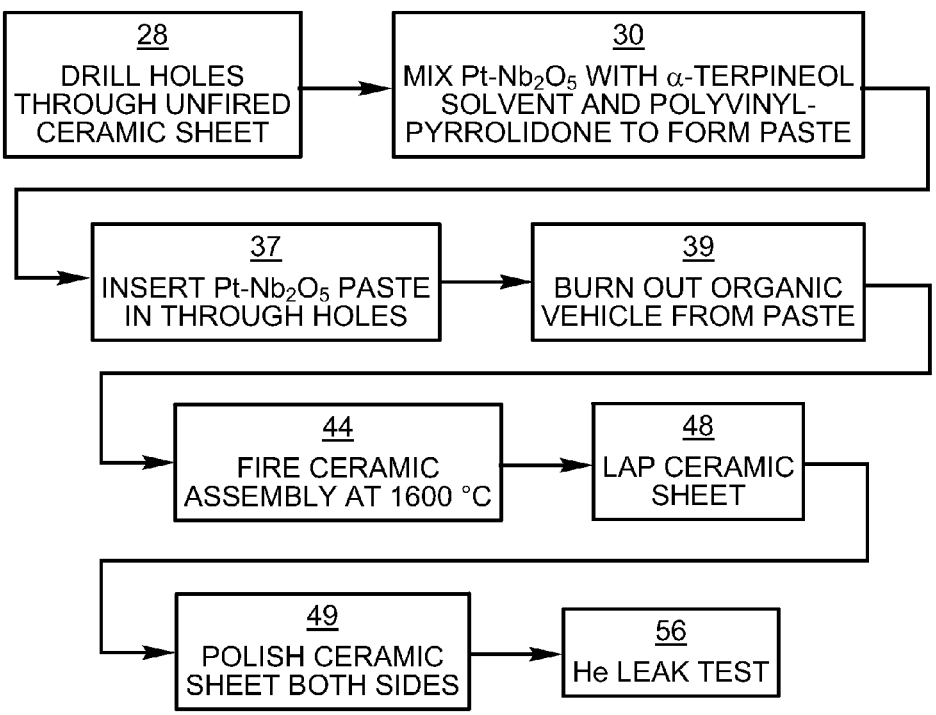
Fig. 3

METHOD OF FORMING HERMETIC VIAS UTILIZING METAL-METAL OXIDES

CROSS REFERENCE TO RELATED APPLICATION

This is a divisional application of application Ser. No. 11/694,774 filed on Mar. 30, 2007. Additionally, U.S. patent application Ser. No. 11/694,774 claims the benefit of U.S. Provisional Application Ser. No. 60/744,992, filed on Apr. 17, 2006.

BACKGROUND OF THE INVENTION

1. Field of the Invention

This invention relates to a hermetic via in a ceramic substrate, which may be used in implantable devices.

2. Description of Related Art Including Information Disclosed Under 37 CFR 1.97 and 1.98

Various approaches are known for fabricating hermetically sealed electrical circuit housings suitable for extended operation in corrosive environments, e.g., in medical devices implanted in a patient's body. For such applications, a housing may be formed of biocompatible and electrochemically stable materials and typically may include a wall containing multiple hermetic electrical feedthroughs. A hermetic electrical feedthrough is comprised of electrically conductive material which extends through and is hermetically sealed in the wall material.

One known approach for forming feedthroughs uses platinum thick film vias through 92% or 96% aluminum oxide ceramic with significant glass content. This glass content is susceptible to hydroxide etching that may occur as an electrochemical reaction to an aqueous chloride environment such as is found in the human body. This will, over extended time, compromise the hermeticity and structural stability of the feedthrough. Typically, 92% aluminum oxide ceramic is used in conjunction with a platinum/glass or platinum/aluminum oxide thick film paste. These material systems are generally formulated to optimize coefficient of thermal expansion mismatches and achieve a hermetic feedthrough. However, use of metal/insulator frit significantly reduces the conductive volume of the feedthrough limiting the current carrying capacity of the feedthrough.

An alternative approach uses an assembled pin feedthrough consisting of a conductive pin that is bonded chemically at its perimeter through brazing or the use of oxides, and/or welded, and/or mechanically bonded through compression to a ceramic body. Typically, gold is used as a braze material that wets the feedthrough pin and the ceramic body resulting in a hermetic seal. Wetting to the ceramic body requires a deposited layer of metal such as titanium. This layer acts additionally as a diffusion barrier for the gold.

It is also known that tungsten, platinum or platinum-glass form vias in ceramics, such as alumina or zirconia. However, it has been difficult to form hermetic seals with the ceramic substrates, since platinum is a relatively soft material that shrinks from the walls of the via during sintering. The use of a glass frit with the platinum, for example, generally yields weak vias that do not bond well with the platinum. It is possible to obtain a hermetic via after firing, only to lose hermeticity during post-processing, such as soldering or brazing, due to the formation of worm holes in the via.

The shortcoming of using glass frit in the conductive materials is related to (1) the low electrical conductivity of the glass and (2) the weak bond between the via and the ceramic substrate after heat treatment. One alternative to glass frit binder involves using a metal oxide as the binder. Alternately the glass frit is replaced with an active metal as the bonding agent.

Alternative feedthrough approaches use a metal tube co-fired with a green ceramic sheet. The hermeticity of the metal/ceramic interface is achieved by a compression seal formed by material shrinkage when the assembly is fired and cooled. The use of a tube inherently limits the smallest possible feedthrough to the smallest available tubing. Acceptable results have been reported when using tubes having a diameter greater than 0.040 inches in ceramic substrates that are at least 0.070 inches thick.

BRIEF DESCRIPTION OF THE SEVERAL VIEWS OF THE DRAWINGS

FIG. 1 illustrates a top view of a finished feedthrough assembly in accordance with the present invention comprised of a thin ceramic sheet having electrically conductive wires extending therethrough.

FIG. 2 is a sectional view taken substantially along the plane 2-2 of FIG. 1 showing the wire ends flush with the surfaces of the thin ceramic sheet.

FIG. 3 is a flow diagram illustrating a preferred series of process steps for fabricating a feedthrough assembly in accordance with the present invention.

DETAILED DESCRIPTION OF THE INVENTION

Attention is directed to FIGS. 1 and 2, where FIG. 2 is a sectional view taken along the plane 2-2 of FIG. 1, which depict a preferred feedthrough assembly 8, in accordance with the present invention, comprising a thin substrate 10 of ceramic material having multiple electrical feedthroughs, known as vias 12, extending therethrough terminating flush with the upper surface 14 and the lower surface 16 of substrate 10. The substrate 10 typically comprises a wall portion of a housing (not illustrated) for accommodating electronic circuitry. The vias 12 function to electrically connect devices external to the housing, e.g., adjacent to surface 14, to electronic circuitry contained within the housing, e.g., adjacent to surface 16.

The vias 12, in accordance with the invention, are intended to function in corrosive environments, e.g., in medical devices intended for implantation in a patient's body. In such applications, it is generally critical that the device housing be hermetically sealed which, of course, requires that all feedthroughs in the housing wall also be hermetic. In such applications, it is also generally desirable that the weight and size of the housing be minimized and that all exposed areas of the housing be biocompatible and electrochemically stable. Biocompatibility assures that the implanted device has no deleterious effect on body tissue. Electrochemical stability assures that the corrosive environment of the body has no deleterious effect on the device. Ceramic and platinum materials are often used in implantable medical devices because they exhibit both biocompatibility and electrochemical stability.

The present invention is directed to providing vias 12 compatible with thin ceramic substrate 10, which may be comprised of zirconium oxide, but which is preferably comprised of aluminum oxide having a finished thickness of less than about 0.040 inches, where the vias 12 are hermetic, biocompatible, and electrochemically stable. In accordance with a preferred embodiment of the invention, the ceramic substrate 10 is formed of 99% aluminum oxide and the vias 12 have a diameter less than about 0.020 inches.

The vias 12 are comprised a noble metal, in a preferred embodiment the noble metal is platinum, platinum-iridium, platinum-niobium or platinum-tantalum that premixed with a particulate phase comprised of niobium pentoxide, ($Nb_2O_5$), which is known to be an electrical insulator, compared to niobium oxide (NbO), which is electrically conductive. The niobium pentoxide is added in an amount of 1% to 10% by weight in the mixture and in a preferred embodiment about 8% by weight. In a preferred embodiment the via 12 composition particle size is suitable for application by screen printing, dipping or spraying. The niobium pentoxide is a distinct phase that prevents or minimizes shrinkage of the via 12 during thermal processing while binds to both the metal contents in the via 12 and ceramic substrate 10, thereby keeping the via 12 in contact with the walls of the ceramic substrate 10 and thus assuring a hermetic seal in the finished component. An organic vehicle which contains alpha terpineol solvent and about 5% of polyvinylpyrrolidone is used to form the paste.

Attention is now directed to FIG. 3 which depicts the preferred process steps for fabricating the finished feedthrough assembly 8 illustrated in FIGS. 1 and 2.

Initially, an unfired ceramic substrate, preferably of greater than about 99% aluminum oxide, is selected. The unfired ceramic substrate is preferably formed by rolling unfired ceramic material to impart shear forces to agglomerates in the moist ceramic slurry. This rolling process breaks down these agglomerates and produces a substrate of dense uniformly distributed fine aluminum oxide particulate.

In Step 28 through holes are drilled in the unfired ceramic substrate. In Step 30 the platinum particulate and niobium pentoxide are mixed with alpha-terpineol solvent and polyvinylpyrrolidone to form a paste. These through holes are filled with a noble metal containing paste, which in a preferred embodiment is a platinum paste that contains niobium pentoxide particulate, step 37. The organic vehicle binder in the ceramic paste is burned out in air in step 39 prior to firing the assembly in vacuum or inert gas.

In Step 44 of FIG. 3 the ceramic assembly is fired. The maximum firing temperature is sufficient to sinter the material of the ceramic sheet 20 but insufficient to melt the material of the ceramic paste. Assuming a ceramic substrate of greater than about 99% aluminum oxide and high purity platinum paste, a firing temperature of 1600° C. satisfies this requirement. An exemplary preferred firing schedule includes ramping the assembly up to 600° C. at a rate of 10° C./minute, then ramping up to the firing temperature of about 1600° C. at a rate of about 5° C./minute, followed by a one hour dwell at temperature and then a cool-to-room-temperature interval.

As the sintered ceramic substrate cools, the hole diameter decreases. After densification and upon cooling, little shrinkage of the paste occurs in via 12 because the niobium pentoxide particulate maintains its volume during the cooling cycle. This action produces a sound hermetic metal/ceramic interface. The niobium pentoxide has a maximum particle size of about 44 micron or less. It has been learned that the niobium pentoxide is a bonding agent that replaces the glass phase and that results in a good bond between the fired via 12 and the ceramic substrate 10.

In Step 48 of FIG. 3 the upper 14 and lower surfaces 16 of the fired ceramic substrate 10 are lapped or ground to smooth the surfaces, in order to smooth the via 12 surface. In step 49 both sides of the ceramic sheet 8 are polished. The thickness of the finished sheet, and wire lengths, in a preferred embodiment is typically less than about 0.012 inches.

In step 56 the vias 12 are leak tested with helium.

From the foregoing, it should now be appreciated that electrical feedthrough assemblies and fabrication methods therefor have been described suitably for use in medical devices intended for implantation in a patient's body. Although a specific structure and fabrication method has been described, it is recognized that variations and modifications will occur to those skilled in the art coming within the spirit and scope of the invention as defined by the appended claims.

What is claimed is:

1. A method of forming a hermetic via electrical feedthrough in a ceramic substrate comprising the steps of:
   selecting a glass-free electrically conductive paste;
   selecting 1 to 10 weight percent niobium pentoxide particulate phase;
   selecting a noble metal particulate phase comprising 90 to 99 weight percent platinum metal particulate phase;
   selecting an unfired ceramic substrate having an upper surface and a lower surface and containing through holes that extend from said upper surface to said lower surface;
   inserting said glass-free electrically conductive paste comprising said noble metal particulate phase, said niobium pentoxide particulate phase, and an organic vehicle in said through holes;
   removing said organic vehicle binder by heating said unfired ceramic substrate in air;
   firing said ceramic substrate and paste filled through holes at 1600° C. forming a hermetic, densified, glass-free, worm hole free electrically conductive via comprised of said glass-free electrically conductive paste;
   cooling said ceramic substrate to room temperature; and
   polishing said ceramic substrate to smooth said upper surface and said lower surface.

2. The method according to claim 1, wherein a step of selecting an unfired ceramic substrate is selecting said ceramic substrate comprised of greater than 99% aluminum oxide.

3. The method according to claim 1, further comprising a step of helium leak testing said hermetic via in said ceramic substrate.

* * * * *

UNITED STATES PATENT AND TRADEMARK OFFICE
Certificate

Patent No. 8,043,454 B1                                                    Patented: October 25, 2011

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Guangqiang Jiang, Valencia, CA (US); Attila Antalfy, Santa Clarita, CA (US); Gary D. Schnittgrund, Granada Hills, CA (US); and Brian Lasater, Wenatchee, WA (US).

Signed and Sealed this First Day of July 2014.

JENNIFER MCNEIL
*Supervisory Patent Examiner*
Art Unit 3992
Technology Center 3900